United States Patent
Karasawa et al.

(10) Patent No.: US 7,380,456 B2
(45) Date of Patent: Jun. 3, 2008

(54) 3-DIMENSIONAL ULTRASONOGRAPHIC DEVICE

(75) Inventors: Hirokazu Karasawa, Yokohama (JP); Motohisa Abe, Ibaraki-ken (JP); Yoshino Ito, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 217 days.

(21) Appl. No.: 10/560,436

(22) PCT Filed: Jun. 16, 2004

(86) PCT No.: PCT/JP2004/008445

§ 371 (c)(1),
(2), (4) Date: Dec. 14, 2005

(87) PCT Pub. No.: WO2004/111630

PCT Pub. Date: Dec. 23, 2004

(65) Prior Publication Data

US 2006/0123912 A1    Jun. 15, 2006

(30) Foreign Application Priority Data

Jun. 17, 2003  (JP)  ............................. 2003-172024
Oct. 16, 2003  (JP)  ............................. 2003-356958

(51) Int. Cl.
*G01N 29/04*    (2006.01)
*G01N 29/24*    (2006.01)

(52) U.S. Cl. ......................................... 73/625; 73/643

(58) Field of Classification Search ......... 73/596–600, 73/602, 620–626, 614, 618, 611, 637, 643
See application file for complete search history.

(56) References Cited

U.S. PATENT DOCUMENTS

| 4,817,434 A | 4/1989 | Anderson |
| 5,060,201 A | 10/1991 | Ishikawa et al. |
| 5,475,613 A | 12/1995 | Itoga et al. |
| 5,877,830 A * | 3/1999 | Shimada et al. ............ 349/110 |
| 6,283,918 B1 | 9/2001 | Kanda et al. |

(Continued)

FOREIGN PATENT DOCUMENTS

JP    06-050744 A    2/1994

(Continued)

OTHER PUBLICATIONS

Satoshi Nagai et al., "Development of Visual Inspection Technique Under Sodium in FBR," The Thermal and Nuclear Power, vol. 47, No. 8, Aug. 15, 1996, pp. 846-852.

*Primary Examiner*—Helen C. Kwok
(74) *Attorney, Agent, or Firm*—Foley & Lardner LLP

(57) ABSTRACT

This three-dimensional ultrasonographic device is a three-dimensional ultrasonographic device having a matrix sensor 9 composed of a plurality of piezoelectric vibrators which are formed independently and arranged in a matrix, and it generates 3D imaging data based on reflected echoes of an ultrasonic wave obtained from the matrix sensor 9 and processes display images into two-dimensional images. Furthermore, this three-dimensional ultrasonographic imaging device connects a plurality of imaging data that are obtained while the matrix sensor 9 is moved, according to the position of the matrix sensor 9, thereby realizing imaging of a defect 14 for quantitative and intuitive judgment and enabling automatic judgment of the inspection. In addition, in imaging, an area other than an inspection area of the inspection object is masked, which realizes improved image quality.

18 Claims, 6 Drawing Sheets

U.S. PATENT DOCUMENTS

| | | | |
|---|---|---|---|
| 6,883,362 B2 * | 4/2005 | Ogawa | 73/1.86 |
| 7,090,642 B2 * | 8/2006 | Satoh | 600/447 |
| 7,094,203 B2 * | 8/2006 | Inoue et al. | 600/439 |
| 7,196,969 B1 * | 3/2007 | Karazincir | 367/50 |
| 2004/0024320 A1 | 2/2004 | Karasawa et al. | |

FOREIGN PATENT DOCUMENTS

| | | |
|---|---|---|
| JP | 06-102258 A | 4/1994 |
| JP | 06-294779 A | 10/1994 |
| JP | 10-062396 A | 3/1998 |
| JP | 11-118775 A | 4/1999 |
| JP | 11-164833 A | 6/1999 |
| JP | 2002-048867 A | 2/2002 |
| JP | 2003-149213 A | 5/2003 |
| WO | WO 92/18862 A1 | 10/1992 |
| WO | WO 03/042686 A1 | 5/2003 |

* cited by examiner

3-DIMENSIONAL ULTRASONOGRAPHIC DEVICE

TECHNICAL FIELD

The present invention relates to a three-dimensional ultrasonographic device that three dimensionally (3D) visualizes a defect, a void, a foreign substance such as an oxide film, and a peeling state of a joint portion in a structure to be inspected, by using ultrasonic waves transmitted/received by a large number of two-dimensionally arranged piezoelectric vibrators.

BACKGROUND ART

There has been proposed an ultrasonic inspection device using an ultrasonic transducer composed of a plurality of piezoelectric vibrators that are formed independently from each other and arranged in a matrix (see, for example, Patent document 1). With the conventional ultrasonic inspection device, a layer structure having a plurality of different acoustic characteristics, and a defect, a void, and peeling in an inspection object having a curved surface can be visualized by using ultrasonic waves, but since judgment on the result imaged by the ultrasonic waves relies on eyes, it is difficult to automatically judge the result and to recognize the positional relation with the inspection object.

Such a conventional ultrasonic inspection device has the following problems.

[1] Objective and quantitative inspection is difficult since internal inspection relies on a person's observation of the imaged result.
[2] Brightness of an image varies at different depths of the inspection object due to the influence of a surface-reflected wave in the inspection object, the attenuation of the ultrasonic wave in the inspection object, and the like.
[3] Continuous imaging of a wide area is not possible due to the limited size of the ultrasonic transducer.
[4] If the periphery of an inspection area of the inspection object is uneven, the ultrasonic wave reflected on the uneven portion of the periphery deteriorates image quality of an internal image of the inspection object.
[5] It is not possible to automatically determine whether abnormality exists or not, based on position and shape information of the defect obtained from the three-dimensional imaging of the interior of the inspection object.

[Patent document 1] Japanese Patent Laid-open Application No. 2003-149213

DISCLOSURE OF THE INVENTION

The present invention was made in order to solve the above-described problems and its object is to provide a three-dimensional ultrasonographic device that achieves improved accuracy of internal inspection using an ultrasonic wave, a wider inspection area, and automatic judgment of the inspection.

A three-dimensional ultrasonographic device of the present invention includes: an ultrasonic transducer composed of a plurality of piezoelectric vibrators; a vibrator selecting part which causes an arbitrary one of the plural piezoelectric vibrators to generate an ultrasonic wave; a signal detecting circuit which selectively detects electrical signals that the plural piezoelectric vibrators generate when the piezoelectric vibrators receive echoes of the ultrasonic wave, which is generated by the piezoelectric vibrator selected by the vibrator selecting part to pass through an acoustic medium and to be reflected in an inspection object; a signal processing part which generates three-dimensional image data by aperture synthesizing from the electrical signals detected by the signal detecting circuit, in correspondence to meshes in a three-dimensional imaging area set in the inspection object; and a display processing part which has: a function of changing brightness or transparency with which respective meshes set in the three-dimensional area, according to values of the three-dimensional imaging data generated by the signal processing part; and a function of applying masking or image brightness correction to an image of an unnecessary portion of the three-dimensional imaging data, by multiplying the value of the three-dimensional imaging data by a value set according to a three-dimensional coordinate position (X, Y, Z).

The present invention can provide a three-dimensional ultrasonographic device that achieves improved accuracy of internal inspection using an ultrasonic wave, a wider inspection area, and automatic judgment of the inspection.

BEST MODE FOR CARRYING OUT THE INVENTION

Figure 1:
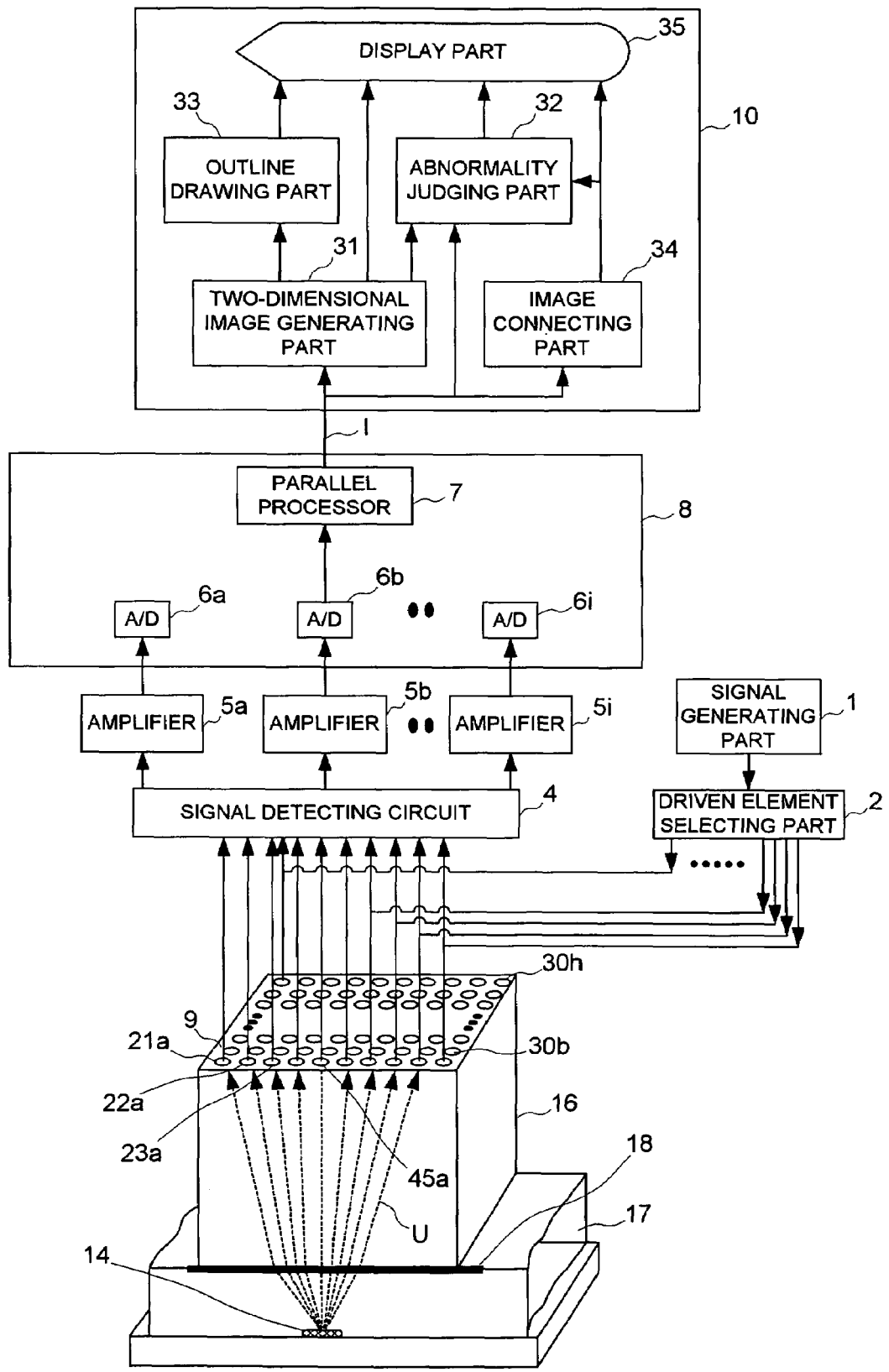
FIG. 1 is a diagram showing a whole configuration of a three-dimensional ultrasonographic device of one embodiment according to the present invention.

A three-dimensional ultrasonographic device of this embodiment includes: a signal processing part which generates three-dimensional imaging data corresponding to meshes in a three-dimensional imaging area set in an inspection object; and; a display processing part which has: a function of changing brightness or transparency with which respective meshes set in the three-dimensional area, according to values of the three-dimensional imaging data generated by the signal processing part; and a function of applying masking or image brightness correction to an image of an unnecessary portion of the three-dimensional imaging data, by multiplying the value of the three-dimensional imaging data by a value set according to a three-dimensional coordinate position (X, Y, Z).

The display processing part includes a two-dimensional image generating part which sees through the three-dimensional imaging data from totally three directions, namely, a direction from a front face as viewed from an ultrasonic transducer, and directions vertical to two side faces perpendicular to the front face, and projects, on a two-dimensional plane, data with the largest value out of imaging data stacked in each of the see-through directions out of the three-dimensional imaging data to thereby generate three two-dimensional images in the respective directions.

The three-dimensional ultrasonographic device further includes an outline drawing part which draws an outline of a shape of the inspection object so as to overlay the outline on the three two-dimensional images generated by the two-dimensional image generating part.

The three-dimensional ultrasonographic device further includes an outline drawing part which draws three-dimensional shapes of an outline of the inspection object and a post-processed portion, by overlaying the three-dimensional imaging data generated by the signal processing part on the three-dimensional imaging area.

The three-dimensional ultrasonographic device further includes an abnormality judging part which compares the values of the three-dimensional imaging data corresponding to the meshes in the three-dimensional imaging area with a predetermined set value to output the mesh whose value is equal to or larger than the set value, and automatically calculates a ratio of the number of the outputted meshes whose values are equal to or larger than the set value to judge that abnormality exists when an automatically calculated value becomes equal to or larger than a prescribed value.

The three-dimensional ultrasonographic device includes an abnormality judging/displaying part which compares values of the two-dimensional image data generated by the two-dimensional image generating part with a predetermined set value to output the mesh whose value is equal to or larger than the set value, and compares three-dimensional coordinates of the outputted imaging mesh with preset three-dimensional shape information on an outline shape of the inspection object or on a post-processed portion, thereby detecting whether or not an interference between a defect position and the post-processed portion exists in the inspection object to display a result of the detection.

The three-dimensional ultrasonographic device further includes an abnormality judging/displaying part which, when the imaging mesh whose value exceeds the predetermined set value is selected from the two-dimensional image data generated by the two-dimensional image generating part, automatically calculates an area of an abnormal portion based on an adjacency state of the selected imaging mesh and judges whether or not the automatically calculated area of the abnormal portion is equal to or larger than a prescribed value to display a result of the judgment.

The three-dimensional ultrasonographic device includes an abnormality judging/displaying part which compares the values of the three-dimensional imaging data corresponding to the meshes in the three-dimensional imaging area with a predetermined set value to output the mesh whose value is equal to or larger than the set value, and compares three-dimensional coordinates of the outputted mesh with preset three-dimensional shape information on an outline shape of the inspection object and on a post-processed portion, thereby detecting whether or not an interference between a defect position and the post-processed portion exists in the inspection object to display a result of the detection.

The three-dimensional ultrasonographic device includes a unit which, when the abnormality judging/displaying part outputs the mesh whose value is equal to or larger than the set value from the three-dimensional imaging data, automatically calculates a volume of the abnormal portion based on an adjacency state of the outputted imaging data and judges whether or not an area of the abnormal portion is equal to or larger than a prescribed value to display a result of the judgment.

The three-dimensional ultrasonographic device includes: a mechanism part which mechanically drives the transducer and detects a movement position of the transducer; an image connecting part connecting the plural imaging data that are detected each time the transducer is moved by the mechanism part; and a display part displaying images connected by the image connecting part.

In this three-dimensional ultrasonographic device, the ultrasonic wave is generated by an arbitrary one of the plural piezoelectric vibrators of the ultrasonic transducer. The signal detecting circuit selectively detects electrical signals that the plural piezoelectric vibrators generate when the piezoelectric vibrators receive echoes of the ultrasonic wave, which is generated by the piezoelectric vibrator to pass through an acoustic medium made of solid or liquid and to be reflected in an inspection object made of a layer with a planar or curved boundary and with a single acoustic characteristic or a plurality of acoustic characteristic.

Then, the signal processing part generates the three-dimensional imaging data by aperture synthesizing from the electrical signal detected by the signal detecting circuit, in correspondence to the meshes in the three-dimensional imaging area set in the inspection object and outputs the three-dimensional imaging data to the display processing part.

The display processing part changes brightness or transparency with which respective meshes set in the three-dimensional area, according to values of the three-dimensional imaging data generated by the signal processing part.

Further, the display processing part applies masking or image brightness correction to the image of the unnecessary portion of each of the three-dimensional imaging data by multiplying the value of the three-dimensional imaging data by the value set according to the three-dimensional coordinate position (X, Y, Z).

Thus, the three-dimensional imaging data synthesized in the three-dimensional ultrasonographic device having the ultrasonic transducer and the display images are processed, and the plural imaging data obtained while the ultrasonic transducer is moved are connected according to the position of the ultrasonic transducer, so that it is possible to image a defective portion of the inspection object for more quantitative and intuitive judgment. Further, in imaging, an area other than the inspection area of the inspection object is masked, so that image quality can be improved.

The three-dimensional coordinates of the imaging mesh whose value exceeds the set value out of the three-dimensional imaging data generated by the three-dimensional ultrasonographic device or out of the two-dimensional image data generated by the two-dimensional image generating part are compared with the three-dimensional shape information on the outline shape of the inspection object and on the post-processed portion, and based on the comparison, it is judged whether or not the defective portion interferes with the post-processed portion, and the area of the abnormal portion is automatically calculated based on whether or not the adjacency of the imaging mesh exists, so that the automatic judgment of the inspection is enabled.

Further, the plural imaging data obtained by providing the mechanism part which is capable of moving the ultrasonic transducer while detecting the position thereof are connected according to the position of the ultrasonic transducer, so that a wide area can be imaged.

Further, a masking part having an aperture at a position corresponding to the inspection area of the surface of the inspection object is provided on the surface of the inspection object, so that it is possible to prevent image quality of the internal image from deteriorating due to the ultrasonic wave reflected on the uneven portion of the periphery of the inspection area.

Hereinafter, an embodiment of the present invention will be described with reference to the drawings.

FIG. 1 is a diagram showing a configuration of a three-dimensional ultrasonographic device of one embodiment according to the present invention.

As shown in FIG. 1, the three-dimensional ultrasonographic device has: a signal generating part 1; a driven element selecting part 2; a matrix sensor 9 as an ultrasonic transducer; a signal detecting circuit 4; a signal processing part 8 which is a central processor and is composed of amplifiers 5a, 5b to 5i, A/D converters 6a, 6b to 6i, and a parallel processor 7; a display processing device 10; and so on. On a surface of the matrix sensor 9, an acoustic propagation medium 16 is closely attached. The matrix sensor 9 receives an ultrasonic wave U reflected from a defect 14 in an inspection object (object to be irradiated with the ultrasonic wave) 17 via the acoustic propagation medium 16 and a couplant 18. Incidentally, if the acoustic propagation medium 16 is liquid such as, for example, water, the couplant 18 is not necessary.

The matrix sensor 9 is composed of a plurality of piezoelectric vibrators 21a, 22a, 23a to 29a, 30a, 30b to 30h each made of a piezoelectric element, which are arranged in a matrix, and the driven element selecting part 2 selects and determines one to be driven out of the piezoelectric vibrators 21a and so on, and a driving signal from the signal generating part 1 is led thereto via an electrical lead. Further, electrical signals generated by the piezoelectric vibrators 21a and so on are led to the signal detecting circuit 4 via electrical leads. When any of the piezoelectric vibrators 21a and so on is electrically driven, an ultrasonic wave is generated owing to its property as a piezoelectric substance, and the generated ultrasonic wave reaches the defect 14 in the inspection object 17 via the acoustic propagation medium 16. Ultrasonic echoes U reflected on the defect 14 are inputted to the piezoelectric vibrators 21a and so on again via the acoustic propagation medium 16, so that the piezoelectric vibrators 21a and so on generate the electrical signals.

The signal generating part 1 generates a pulsed or continuous driving signal so as to cause the piezoelectric vibrators 21a and soon to generate the ultrasonic waves. The generated driving signal is inputted to the driven element selecting part 2 serving as a vibrator selecting part. The driven element selecting part 2 selects one or plural ones to be driven out of the piezoelectric vibrators 21a and so on and inputs the driving signal led from the signal generating part 1 to the selected one/ones of the piezoelectric vibrators 21a and so on to cause the selected one/ones of the piezoelectric vibrators 21a to generate the ultrasonic wave U.

The signal detecting circuit 4 is connected to the plural piezoelectric vibrators 21a and so on and detects the electrical signals generated by the piezoelectric vibrators 21a and soon. The plural ones necessary for inspection out of the detected electrical signals are led to the amplifiers 5a, 5b to 5i in the signal processing part 8 respectively. The signal detecting circuit selectively detects electrical signals that the plural piezoelectric vibrators generate when the piezoelectric vibrators receive echoes of the ultrasonic wave, which is generated by the piezoelectric vibrator to pass through the acoustic propagation medium 16 made of solid or liquid and to be reflected in an inspection object made of a layer with a planar or curved boundary and with a single acoustic characteristic or a plurality of different acoustic characteristics.

The amplifying circuits 5a, 5b-5i amplify the led electrical signals to supply them to the A/D converters 6a, 6b to 6i. The A/D converters 6a, 6b-6i A/D-convert the led electrical signals to lead them to the parallel processor 7 in the signal processing part 8.

The parallel processor 7 in the signal processing part 8 processes the digital signals led from the A/D converters 6a, 6b-6i to generate imaging data I, that is, to visualize a state of the inspection object. Three-dimensional imaging data are generated by aperture synthesizing from the electrical signals detected by the signal detecting circuit 4, in correspondence to meshes in the three-dimensional imaging area set in the inspection object. The imaging data I generated by the parallel processor 7 are outputted to the display processing device 10 and are subjected to visualization/display processing there, and thereafter are displayed on the display part 35.

The display processing device 10 has a two-dimensional image generating part 31, an abnormality judging part 32, an outline drawing part 33, an image connecting part 34, the display part 35, and so on.

The two-dimensional image generating part 31 sees through the three-dimensional imaging data I from totally three directions, namely, a direction from a front face (X-Y plane) as viewed from the ultrasonic transducer, and directions vertical to two side faces (Y-Z plane), (Z-X plane) perpendicular to the front face, and in addition, it projects, on a two-dimensional plane, data with the largest value out of the imaging data stacked in the see-through directions out of the three-dimensional imaging data I in the respective directions to generate three two-dimensional images in the respective directions.

The abnormality judging part 32 compares values of the three-dimensional imaging data I corresponding to the respective meshes in the three-dimensional imaging area 40 with a judgment threshold value T (see FIG. 3) that is preset in a memory or the like to output meshes whose values are equal to or larger than the threshold value T and to automatically calculate a ratio that the number of the outputted meshes whose values are equal to or larger than the threshold value T makes up in the 3D imaging area 40, and determines that abnormality exists when the automatically calculated value is equal to or larger than a prescribed value.

The outline drawing part 33 draws the outline of the shape of the inspection object so as to overlay the outline on the three two-dimensional images generated by the two-dimensional image generating part 31.

The image connecting part 34 connects the plural imaging data that are detected each time the relative position of the matrix sensor 9 and the inspection object is changed by the driving part 73 (see FIG. 6) being a mechanism part. Incidentally, the aforesaid abnormality judging part 32 outputs the meshes whose values are equal to or larger than the threshold value T based on the comparison with the judgment threshold value T (see FIG. 3) that is preset in the memory or the like for the two-dimensional images formed by the aforesaid two-dimensional image generating part 31 and for the connected images generated by the aforesaid image connecting part 34, and automatically calculates the ratio of the number of the outputted meshes whose values are equal to or larger than the threshold value T, and judges that the abnormality exists when the obtained value is equal to or larger than the prescribed value.

The display part 35 displays the imaging data and/or the judgment result inputted from each part, and it displays, for example, the imaging data inputted from the image connecting part 34 and/or the judgment result of the abnormality judging part 32. The display part 35 and the abnormality judging part 32 will be referred to as an abnormality judging/displaying part.

Specifically, the display processing device 10 has a function of changing brightness or transparency with which respective meshes set in the three-dimensional area, according to values of the three-dimensional imaging data I generated by the signal processing part 8. The display processing device 10 also has a function of applying masking or image brightness correction to an image of an unnecessary portion of the three-dimensional imaging data by multiplying the value of the three-dimensional imaging data I generated by the signal processing part 8 by a value that is set according to a three-dimensional coordinate position (Z, Y, Z).

Figure 2A:
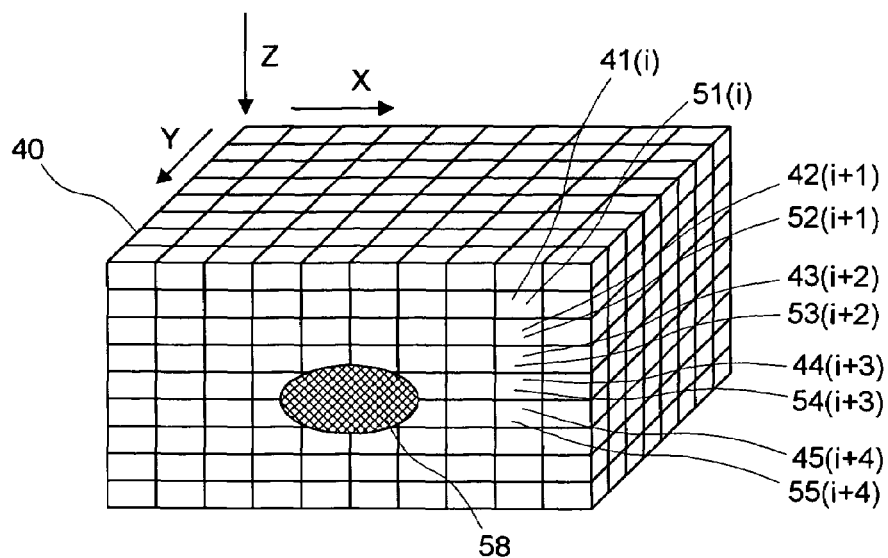
FIG. 2A is a view showing the result of three-dimensional imaging of an inspection object.

The contents of processing where the display processing device 10 displays the aforesaid three-dimensional imaging data I outputted from the signal processing part 8 will be described with reference to FIG. 2A and FIG. 2B. FIG. 2A is a view showing the result of the 3D imaging of the inspection object 17 and FIG. 2B is a chart showing distribution R of reflection intensity of a surface-reflected wave in the 3D imaging area 40 in FIG. 2A.

As shown in FIG. 2A, the three-dimensional imaging data I is an aggregate of imaging data (i)51, imaging data (i+1)52, imaging data (i+2)53, imaging data (i+3)54, imaging data (i+4)55 . . . , and so on which present the reflection intensity of the ultrasonic wave and are stored in correspondence to an imaging cell (i)41, an imaging cell (i+1)42, an imaging cell (i+2)43, an imaging cell (i+3)44, an imaging cell (i+4)45, . . . and so on three-dimensionally arranged in the 3D imaging area 40.

Figure 2B:
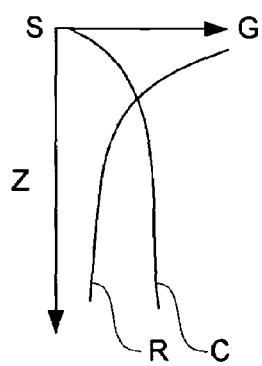
FIG. 2B is a chart showing the distribution of reflection intensity of a surface-reflected wave in a 3D imaging area.

Meanwhile, as for the distribution R of the reflection intensity of the surface-reflected wave, since the ultrasonic wave U is reflected on a surface S (depth Z=0) in the inspection object 17, the reflection intensity in the 3D imaging area 40 becomes higher in the vicinity of the surface, as shown in FIG. 2B, to block an internal image. Therefore, respective values shown by the calibration curve C are added to the imaging data (i)51, imaging data (i+1)52, imaging data (i+2)53, imaging data (i+3)54, imaging data (i+4)55, . . . and so on according to a depth Z to make the reflection intensity in the vicinity of the surface position S small (transparent), whereby it is possible to make image brightness in the vicinity of the surface and brightness of a deep portion uniform. Note that the reference symbol G represents a gain.

Here, an imaging method where the 3D imaging area 40 is seen through in the X, Y, and Z directions for displaying the visualized information in the three-dimensional ultrasonographic device will be described with reference to FIG. 2A to FIG. 2C. Out of the imaging data (i)51, the imaging data (i+1)52, the imaging data (i+2)53, the imaging data (i+3)54, the imaging data (i+4)55, . . . arranged in line in the Z direction as shown in FIG. 2A, the two-dimensional image generating part 31 selects the imaging data with the maximum reflection intensity in the two-dimensional image X-Y 60, namely, imaging data (imax) 57, as shown in, for example, FIG. 2C, to output it to the outline drawing part 33 and the display part 35.

Incidentally, in this example, the two-dimensional image X-Y 60 which is the perspective image from the Z direction is described, but as for perspective images in the X and Y directions, the two-dimensional image generating part 31 selects the image data with the maximum reflection intensity in the same manner as with the perspective image from the Z direction to output them to the display part 35.

Figure 3A:
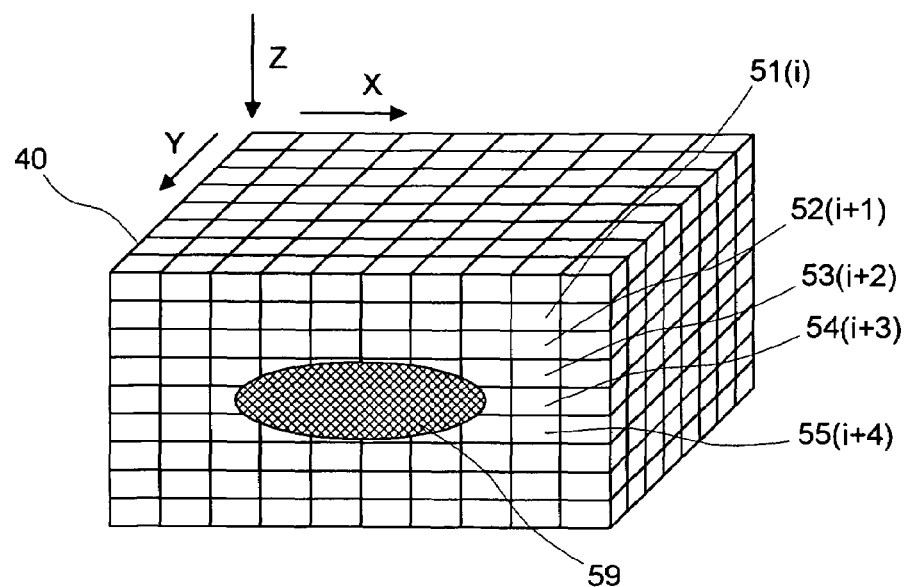
FIG. 3A is a view showing the result of three-dimensional imaging of a defective portion (abnormal portion).
Figure 3B:
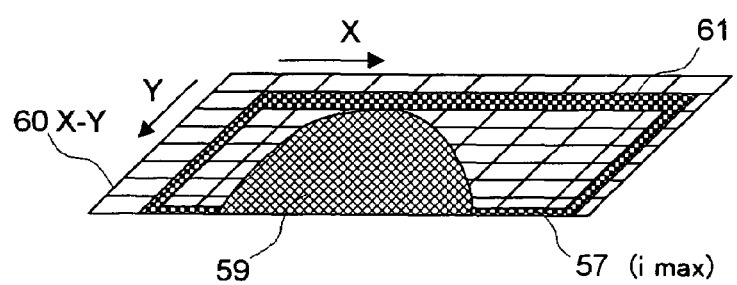
FIG. 3B is a view showing an X-Y two-dimensional image of the defective portion (abnormal portion).
Figure 3C:
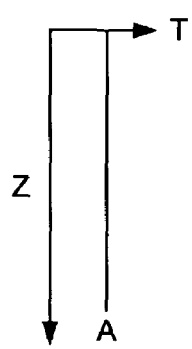
FIG. 3C is a chart showing a characteristic of the imaging data.

FIG. 3A to FIG. 3C are views to illustrate the processing performed in the display processing device 10 for automatically judging an abnormal portion 59 based on the inputted three-dimensional imaging data I. Note that in the drawings, the imaging data I in the 3D imaging area 40 present the reflection intensity of the ultrasonic wave.

Figure 2C:
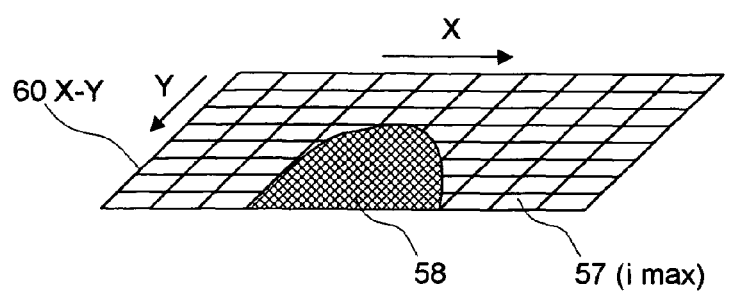
FIG. 2C is a view showing an X-Y two-dimensional image of the imaging data.

When the three-dimensional imaging data I are inputted to the display processing device 10, similarly to the case in FIG. 2A to FIG. 2C, out of the imaging data (i)51, the imaging data (i+1)52, the imaging data (i+2)53, the imaging data (i+3)54, the imaging data (i+4)55, . . . arranged in line in the Z direction as shown in FIG. 3A, the two-dimensional image generating part 31 selects the imaging data with the maximum reflection intensity in the two-dimensional image X-Y 60, namely, imaging data (imax) 57 as shown in FIG. 3B to output it to the outline drawing part 33 and the abnormality judging part 32. Incidentally, as for perspective images in the X and Y directions, the two-dimensional image generating part 31 selects the image data with the maximum reflection intensity in the same manner as with the perspective image from the Z direction. to output them.

In order to make judgment regarding the abnormal portion 59, the abnormality judging part 32 selects (extracts) the imaging data I whose reflection intensity is equal to or larger than a judgment value A based on the judgment threshold value T preset in the memory or the like, and outputs it to the display part 35 for display, and it also calculates a ratio that the abnormal portion 59 makes up in the 3D imaging area 40 based on the result of counting the number of the selected imaging data to judge whether or not the quality of the inspection object 17 is good.

Incidentally, the aforesaid abnormality judging part 32 outputs the meshes whose values are equal to or larger than the threshold value T, based on the comparison with the judgment threshold value T (see FIG. 3C) that is preset in the memory or the like for the two-dimensional images formed by the aforesaid two-dimensional image generating part 31 and for the connected images generated by the aforesaid image connecting part 34, and automatically calculates the ratio that the number of the outputted meshes whose values are equal to or larger than the threshold value T makes up in the 3D imaging area 40, and when the calculated value is equal to or larger than the prescribed value, it judges that the abnormality exists. In the drawing, the reference symbol T represents the threshold value, the reference symbol Z represents the depth, and the reference symbol A represents the judgment value.

The outline drawing part 33 draws a surface shape 61 of the inspection object 17, namely, its outline, on the two-dimensional image X-Y 60 inputted from the two-dimensional image generating part 31. This facilitates determining the position thereof relative to the defect image 58 in the inspection object 17.

An automating method for the abnormal judgment in which the abnormality judging part 32 judges whether or not the abnormality exists based on the two-dimensional imaging result generated by the two-dimensional image generating part 31 of the three-dimensional ultrasonographic device will be described with reference to FIG. 4A to FIG. 4C.

Figure 4A:
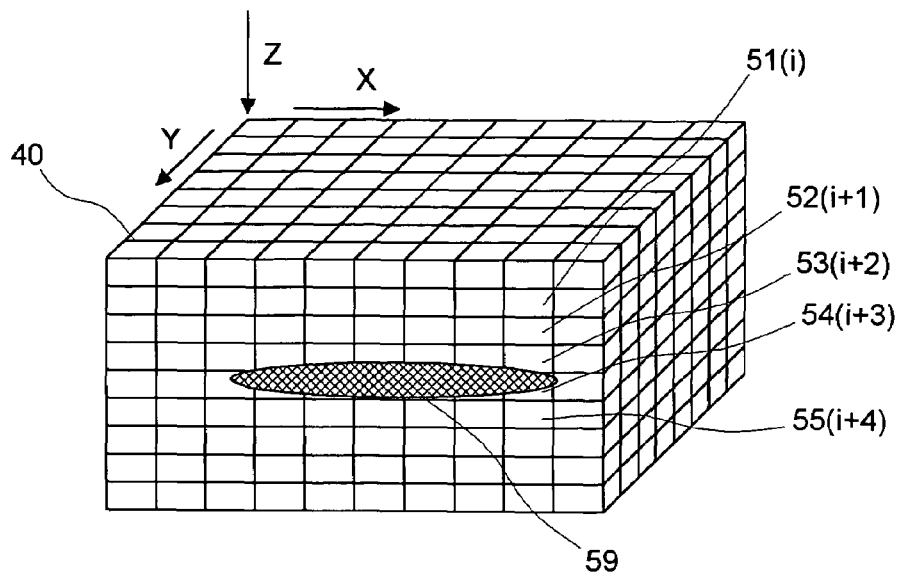
FIG. 4A is a view showing the result of three-dimensional imaging of a defective portion (abnormal portion).
Figure 4B:
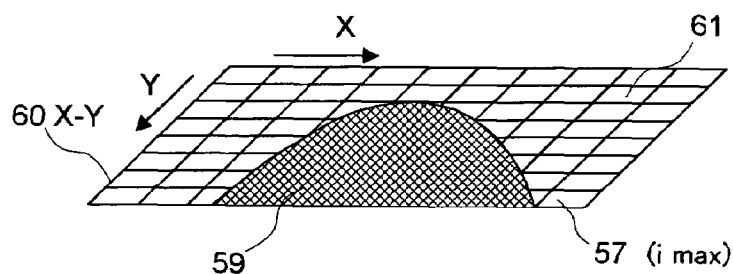
FIG. 4B is a view showing an X-Y two-dimensional image of the defective portion (abnormal portion).

In the two-dimensional image generating part 31, the three-dimensional imaging data (imax) 57, shown in FIG. 4B, in the abnormal portion 59 in the aforesaid two-dimensional image X-Y 60 which is a perspective image from the Z direction is the imaging data (i+3) with the maximum reflection intensity which is extracted from the imaging data (i), the imaging data (i+1), the imaging data (i+2), the imaging data (i+3), . . . arranged in the Z direction in the 3D imaging area 40 shown in FIG. 4A, and therefore, when this imaging data (i+3) is inputted to the abnormality judging part 32, the abnormality judging part 32 determines three-dimensional coordinates of the imaging data (i+3). The abnormality judging part 32 also determines three-dimensional coordinates of the other imaging data of the abnormal portion 59 in the aforesaid two-dimensional image X-Y 60 in the similar manner. The same processing is executed for the perspective images in the X and Y directions.

Figure 4C:
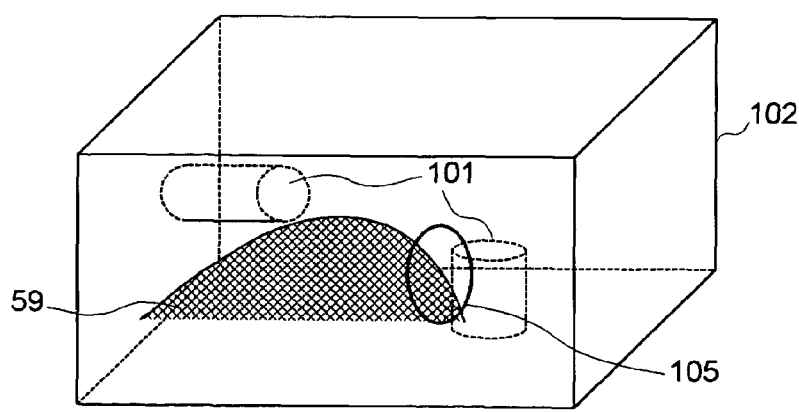
FIG. 4C is a view showing abnormality judgment based on the two-dimensional images.

Then, the abnormality judging part 32 compares post-processing three-dimensional shape information 101 and outline three-dimensional shape information 102 as shown in FIG. 4C which are set in the memory in correspondence to the three-dimensional imaging area 40, with the three-dimensional coordinates of the abnormal portion 59 in the aforesaid two-dimensional image X-Y 60, thereby three-dimensionally judging an interference portion 105 where the interference with a post-processed portion exists.

Further, when making the judgment, the abnormality judging part 32 automatically calculates the area of the abnormal portion based on the judgment on the adjacency state of the determined three-dimensional coordinates of all the imaging data of the abnormal portion 59, namely, based on the judgment on whether or not the imaging data of the abnormal portion 59 are adjacent to the post-processing three-dimensional shape information 101 and the outline three-dimensional shape information 102, and judges whether or not the automatically calculated area of the abnormal portion is equal to or larger than the prescribed value, and based on this judgment result, it judges whether or not the abnormal portion 59 is a defect that cannot be neglected.

The abnormality judging part 32 outputs the aforesaid judgment result to the display part 35, and the display part 35 displays the inputted judgment result.

Figure 5A:
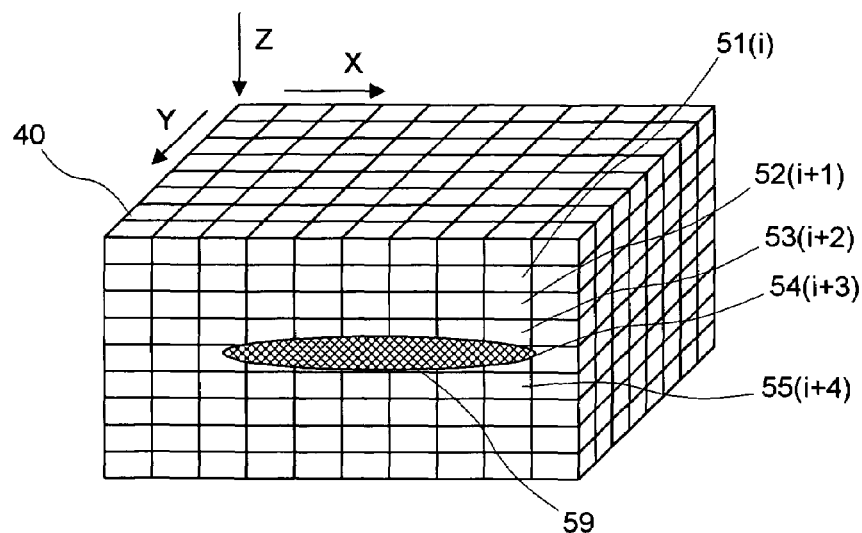
FIG. 5A is a view showing the result of three-dimensional imaging of a defective portion (abnormal portion).
Figure 5B:
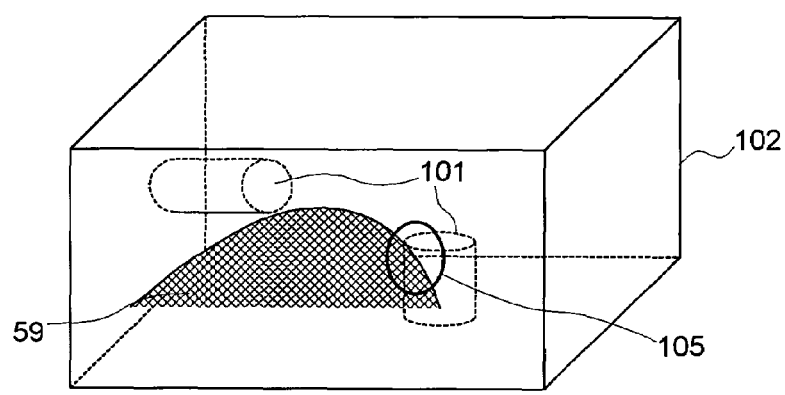
FIG. 5B is a view showing abnormality judgment directly based on the result of the three-dimensional imaging.

Further, as shown in FIG. 5A, the abnormality judging part 32 selects the maximum reflection intensity in the Z direction (as well as in the X and Y directions) shown in FIG. 4B directly from the three-dimensional imaging result of the three-dimensional ultrasonographic device, and compares the post-processing three-dimensional shape information 101 and the outline three-dimensional shape information 102 as shown in FIG. 5B, which are set in the memory in correspondence to the three-dimensional imaging area 40, with the three-dimensional coordinates of the abnormal portion 59 in the aforesaid two-dimensional image X-Y 60, thereby three-dimensionally judging the interference portion 105 between the post-processed portion and the abnormal portion 59.

Further, when making the judgment, the abnormality judging part 32 discriminates the adjacency state of the determined three-dimensional coordinates of all the imaging data of the abnormal portion 59 to automatically calculate the area of the abnormal portion, and it also judges whether or not the automatically calculated area of the abnormal portion is equal to or larger than the prescribed value, and based on this judgment result, it judges whether or not the abnormal portion is a defect that cannot be neglected. The abnormality judging part 32 outputs the judgment result to the display part 35, and the display part 35 displays the inputted judgment result.

Figure 6:
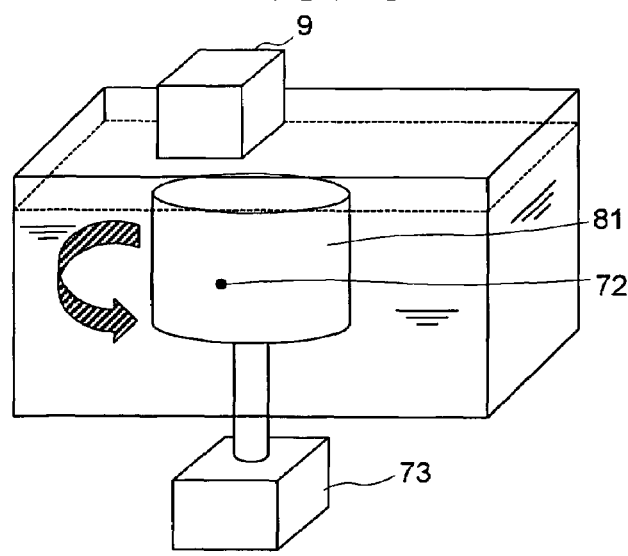
FIG. 6 is a view showing a driving part used for image connection processing.

FIG. 6 is a view to illustrate the image connection processing when the interior of an inspection object 81 larger than a detection area of the matrix sensor 9 (larger than the matrix sensor 9) is imaged. Here, the inspection of the inspection object 81 in a solid cylindrical shape will be described as an example. A driving part 73 mechanically drives the inspection object 81 (or may mechanically drive the matrix sensor 9), and has a sensor detecting the movement position thereof. In this case, the inspection object 81 (or the matrix sensor 9) is driven by the driving part 73 to rotate in the arrow direction.

Meanwhile, the image connecting part 34 of the display processing device 10 connects the plural imaging data that are detected by the sensor every time the relative position of the inspection object 81 and the matrix sensor 9 is changed by the driving part 73, and rearranges and outputs the image data.

Figure 7:
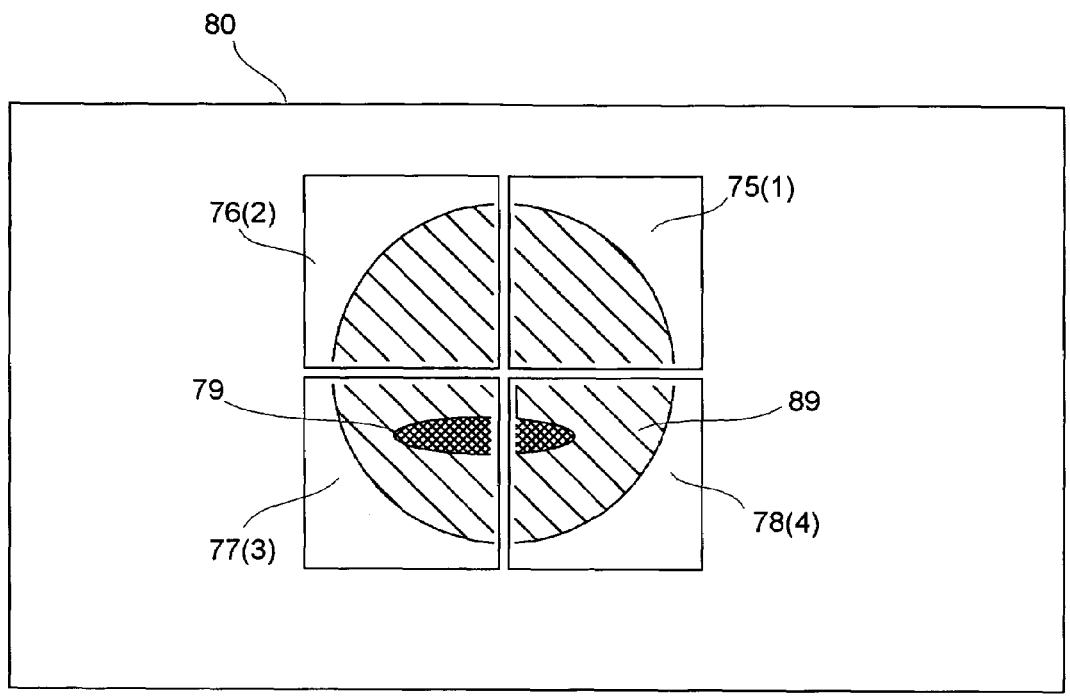
FIG. 7 is a view showing a display screen displaying the result of the image connection processing.

The image data obtained when the inspection object 81 is rotated four times by, for example, 90° at each rotation by the driving part 73 are connected by the image connecting part 34 and are rearranged to be outputted to the display part 35, so that the imaging results of the whole inspection object 81 can be collectively displayed on a display screen 80 as shown in FIG. 7, so that it is possible to obtain the display screen 80 where the position of a defect 72 in the inspection object 81 is easily recognized from a defect image 79 spreading across the plural images. Note that an image (1)75, an image (2)76, an image (3)77, and an image(4)78 are displayed in correspondence to the angles of 90 degrees, 180 degrees, 270 degrees, and 360 degrees.

Incidentally, the abnormality judging part 32 is capable of outputting meshes whose values are equal to or larger than a threshold value T based on the comparison with the judgment threshold value T (see FIG. 3) which is preset in a memory or the like for the connected images generated by the aforesaid image connecting part 34, and automatically calculating a ratio of the number of the outputted meshes whose values are equal to or larger than the threshold value T, and judging that abnormality exists when the calculated value is equal to or larger than a predetermined value.

Figure 8:
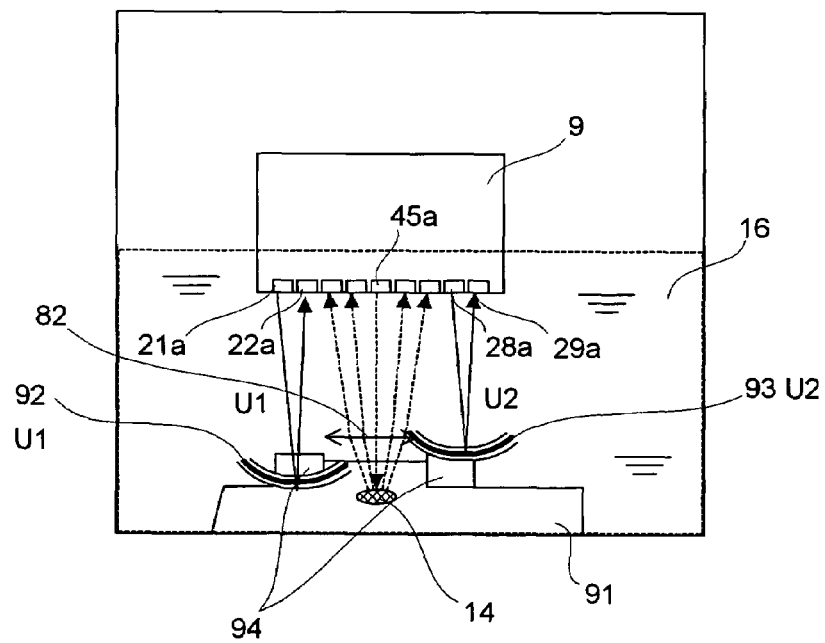
FIG. 8 is a view showing a structural example where a masking part is disposed for image quality improvement.

FIG. 8 is an explanatory view showing a state where a masking part 94 is used to cover an inspection object 91 for imaging the interior thereof, in inspecting the inspection object 91 whose inspection area 82 is in a shape more protruding from the surrounding area. In the drawing, an ultrasonic wave path U1 represents imaging without any masking part 94, and in this case, a drawn image U1 (which becomes a spheroid on a curved surface whose distances from a transmission piezoelectric vibrator 21a and a transmission piezoelectric vibrator 22a are equal) overlaps the interior of the inspection object 91.

Therefore, in this case, the masking part 81 having an aperture at the position corresponding to the inspection area 82 is put over the inspection object 91 to partly cover the surface of the inspection object 91.

A drawn image U2 by an ultrasonic wave path U2 when the surface of the inspection object 91 is covered with such a masking part 94 does not overlap the interior of the inspection object 91, which makes it possible to eliminate a problem that the ultrasonic wave is reflected due to the influence of an uneven portion of the periphery to deteriorate image quality of the internal image of the inspection object when the interior of the inspection object 91 is imaged.

Thus, according to the three-dimensional ultrasonographic device of this embodiment, quantitative inspection is enabled by directly judging values of brightness display and of the imaging data corresponding to the values of the three-dimensional imaging data synthesized from numeral reflected echoes from the interior of the inspection object, the reflected echoes being obtained by the ultrasonic wave transmission/reception by the matrix sensor 9 composed of the plural piezoelectric vibrators independently formed in a matrix.

Further, the values of the imaging data are amplified according to the depth of the three-dimensional imaging area, which enables the correction of the influence of the surface-reflected wave of the inspection object and the correction of the attenuation of the ultrasonic wave in the inspection object. Moreover, the driving part 73 capable of moving the matrix sensor 9 while detecting the position thereof is provided and the plural imaging data are connected according to the position of the matrix sensor 9, which enables imaging of a wider area.

Furthermore, the masking part 94 having the aperture at the position corresponding to the inspection area on the surface of the inspection object is provided so as to cover the surface of the inspection object, which makes it possible to prevent the image quality of the internal image from deteriorating due to the ultrasonic wave reflected on the uneven portion in the periphery of the inspection area.

Furthermore, the values of the imaging data are amplified according to the depth of the three-dimensional imaging area, which enables the correction of the influence of the surface-reflected wave of the inspection object and the correction of the attenuation of the ultrasonic wave in the inspection object.

Moreover, automatic judgment of the inspection becomes possible since the abnormality judging part 32 and the display part 35 are provided, these parts comparing the values of the three-dimensional imaging data corresponding to the meshes in the area of the two-dimensional images generated by the two-dimensional image generating part 31, with the set value preset in the memory, and finding the meshes whose values are equal to or larger than the set value, to compare the three-dimensional coordinates of the found imaging meshes with the three-dimensional shape information on the outline shape of the inspection object and on the post-processed portion, which are preset in the memory, thereby detecting the existence or not of the interference between the defect position and the post-processed portion in the inspection object to display the result thereof.

As a result, it is possible to provide a three-dimensional ultrasonographic device achieving improved accuracy of internal inspection using the ultrasonic wave, a wider inspection area, and automatic judgment of the inspection.

It should be noted that the present invention is not limited to the above-described embodiment.

In the above-described embodiment, the three-dimensional imaging device includes the signal processing part 8 and the display processing device 10, but they may be realized by independent computers respectively.

The computers execute each processing in this embodiment based on programs stored in a storage medium, and may take any structure, for example, may take a form of a single device such as a personal computer, a system in which a plurality of devices are connected via a network, or the like. Further, the computer is not limited to a personal computer (PC), but includes a processor, a microcomputer, and the like included in communication equipment or information processing equipment, and represents all the equipment and devices capable of realizing the functions of the present invention by programs.

The internal structure of the display processing device 10 in the above-described embodiment is realizable by software. The software may be stored in a computer-readable storage medium such as a flexible disk, or may be transmitted on a network such as LAN or the Internet as single software (program). In this case, the computer reads the software (program) stored in the storage medium or the computer downloads the software (program) from a site (server) on LAN or the Internet to install it on a hard disk, so that the processing in the computer becomes possible. In short, the software (program) in the present invention is not limited to that stored in the storage medium independent from the computer, but includes that distributed via a transmission medium such as LAN or the Internet.

Incidentally, a language format and a storage format of the program may be any as long as the program is stored in a storage medium such as a memory, a flexible disk, a hard disk, an optical disk (CD-ROM, CD-R, DVD, or the like), a magneto-optic disk (MO or the like), and a semiconductor memory so as to be computer readable.

Furthermore, each processing for realizing this embodiment may be partly executed by MW (middleware) running on a computer, such as OS (operating system), database management software, or network software, based on an instruction of a program installed in the computer from the storage medium. Further, the storage medium is not limited to a medium independent from the computer, but also includes a storage medium storing or temporarily storing a program transmitted and downloaded via LAN or the Internet. Moreover, the number of the storage media is not limited to one, but a case where the processing in this embodiment is executed from a plurality of media is also embraced in the present invention, and the structure of the storage medium may be any.

INDUSTRIAL APPLICABILITY

The present invention is applicable to the work of inspecting the interior of an inspection object by ultrasonic waves.

What is claimed is:

1. A three-dimensional ultrasonographic device, comprising:
   an ultrasonic transducer composed of a plurality of piezoelectric vibrators;
   a vibrator selecting part which causes an arbitrary one of the plurality of piezoelectric vibrators to generate an ultrasonic wave;
   a signal detecting circuit which selectively detects electrical signals that the plurality of piezoelectric vibrators generate when receiving echoes of the ultrasonic wave, which is generated by the piezoelectric vibrator selected by said vibrator selecting part to be reflected on an inspection object via an acoustic medium;
   a signal processing part which generates three-dimensional imaging data by aperture synthesizing from the electrical signals detected by said signal detecting circuit, in correspondence to meshes in a three-dimensional imaging area set in the inspection object; and
   a display processing part which has: a function of changing brightness or transparency of respective meshes in the three-dimensional imaging area, according to values of the three-dimensional imaging data generated by the signal processing part, that the respective meshes have for the three-dimensional imaging data; a function of applying masking or image brightness correction to an image of an unnecessary portion of the three-dimensional imaging data, by multiplying the value of the three-dimensional imaging data by a value set according to a three-dimensional coordinate position (X, Y, Z), and a two-dimensional image generating part which sees through the three-dimensional imaging data from three directions straight to one another and projects, on a two-dimensional plane, data with the largest value out of imaging data stacked in each of the see-through directions out of the three-dimensional imaging data to thereby generate three two-dimensional images in the respective three directions.

2. The three-dimensional ultrasonographic device as set forth in claim 1, further comprising:

an abnormality judging/displaying part which compares the values of the three-dimensional imaging data corresponding to the meshes in an area of each of the two-dimensional images generated by said two-dimensional image generating part with a predetermined set value to find the mesh whose value is equal to or larger than the set value, and compares three-dimensional coordinates of the found imaging mesh with preset three-dimensional shape information on an outline shape of the inspection object or on a post-processed portion, thereby detecting whether or not an interference between a defect position and the post-processed portion exists in the inspection object to display a result of the detection.

3. The three-dimensional ultrasonographic device according to claim 1, further comprising:

an abnormality judging/displaying part which, when the imaging mesh whose value exceeds the predetermined set value is selected from two-dimensional imaging data generated by said two-dimensional image generating part, automatically calculates an area of an abnormal portion based on an adjacency state of the selected imaging mesh and judges whether or not the automatically calculated area of the abnormal portion is equal to or larger than a prescribed value to display a result of the judgment.

4. The three-dimensional ultrasonographic device as set forth in claim 1, further comprising:

an outline drawing part which draws an outline of a shape of the inspection object so as to overlay the outline on the three two-dimensional images generated by said two-dimensional image generating part.

5. The three-dimensional ultrasonographic device as set forth in claim 1, further comprising:

an outline drawing part which draws three-dimensional shapes of an outline of the inspection object and a post-processed portion, by overlaying the three-dimensional imaging data generated by said signal processing part on the three-dimensional imaging area.

6. The three-dimensional ultrasonographic device as set forth in claim 1, further comprising:

an abnormality judging part which compares the values of the three-dimensional imaging data corresponding to the meshes in the three-dimensional imaging area with a predetermined set value to output the mesh whose value is equal to or larger than the set value, and automatically calculates a ratio of the number of the outputted meshes whose values are equal to or larger than the set value to judge that abnormality exists when an automatically calculated value becomes equal to or larger than a prescribed value.

7. The three-dimensional ultrasonographic device as set forth in claim 1, further comprising:

an abnormality judging/displaying part which compares the values of the three-dimensional imaging data corresponding to the meshes in the three-dimensional imaging area with a predetermined set value to output the mesh whose value is equal to or larger than the set value, and compares three-dimensional coordinates of the outputted mesh with preset three-dimensional shape information on an outline shape of the inspection object and on a post-processed portion, thereby detecting whether or not an interference between a defect position and the post-processed portion exists in the inspection object to display a result of the detection.

8. The three-dimensional ultrasonographic device as set forth in claim 7, further comprising:

a unit which, when said abnormality judging/displaying part outputs the mesh whose value is equal to or larger than the set value from the three-dimensional imaging data, automatically calculates an area of an abnormal portion based on an adjacency state of the outputted imaging data and judges whether or not the area of the abnormal portion is equal to or larger than a predetermined value to display a result of the judgment.

9. The three-dimensional ultrasonographic device as set forth in claim 1, further comprising:

a mechanism part which mechanically drives said transducer and detects a movement position of said transducer;

an image connecting part connecting a plurality of imaging data that are detected each time said transducer is moved by said mechanism part; and a display part displaying images connected by said image connecting part.

10. A three-dimensional ultrasonographic device comprising:

an ultrasonic transducer composed of a plurality of piezoelectric vibrators;

a vibrator selecting part which causes an arbitrary one of the plurality of piezoelectric vibrators to generate an ultrasonic wave;

a signal detecting circuit which selectively detects electrical signals that the plurality of piezoelectric vibrators generate when receiving echoes of the ultrasonic wave, which is generated by the piezoelectric vibrator selected by said vibrator selecting part to be reflected on an inspection object via an acoustic medium;

a signal processing part which generates three-dimensional imaging data by aperture synthesizing from the electrical signals detected by said signal detecting circuit, in correspondence to meshes in a three-dimensional imaging area set in the inspection object;

a display processing part which has: a function of changing brightness or transparency of respective meshes in the three-dimensional imaging area, according to values of the three-dimensional imaging data generated by the signal processing part, that the respective meshes have for the three-dimensional imaging data; and a function of applying masking or image brightness correction to an image of an unnecessary portion of the three-dimensional imaging data, by multiplying the value of the three-dimensional imaging data by a value set according to a three-dimensional coordinate position (X, Y, Z); and a masking part which has an aperture at a position corresponding to an inspection area and which covers a surface of the inspection object, with the aperture being set on the inspection area of the inspection object.

11. The three-dimensional ultrasonographic device as set forth in claim 1, wherein the plurality of piezoelectric vibrators composing said ultrasonic transducer are arranged in a matrix.

12. The three-dimensional ultrasonographic device as set forth in claim 1,
wherein the plurality of piezoelectric vibrators composing said ultrasonic transducer are arranged in line.

13. The three-dimensional ultrasonographic device as set forth in claim 1,
wherein said acoustic medium is solid.

14. The three-dimensional ultrasonographic device as set forth in claim 1,
wherein said acoustic medium is liquid.

15. The three-dimensional ultrasonographic device, as set forth in claim 1,
wherein the inspection object has a planar boundary.

16. The three-dimensional ultrasonographic device as set forth in claim 1,
wherein the inspection object has a curved boundary.

17. The three-dimensional ultrasonographic device as set forth in claim 1,
wherein the inspection object is made of a layer having a single acoustic characteristic.

18. The three-dimensional ultrasonographic device as set forth in claim 1,
wherein the inspection object is made of a layer having a plurality of acoustic characteristics.

* * * * *